United States Patent [19]

Chase

[11] Patent Number: 5,013,403

[45] Date of Patent: May 7, 1991

[54] PROCESS FOR CONTINUOUS DETERMINATION OF PAPER STRENGTH

[75] Inventor: Lee M. Chase, Los Gatos, Calif.

[73] Assignee: Measurex Corporation, Cupertino, Calif.

[21] Appl. No.: 106,828

[22] Filed: Oct. 5, 1987

[51] Int. Cl.$^5$ .......................... D21F 7/06; D21F 9/00; D21F 11/00

[52] U.S. Cl. ..................................... 162/49; 162/198; 162/253; 162/254; 162/263

[58] Field of Search ................. 162/263, 198, 49, 252, 162/253, 254, 258, DIG. 11, DIG. 6, 256, 259

[56] References Cited

U.S. PATENT DOCUMENTS

| | | | |
|---|---|---|---|
| 2,215,329 | 9/1940 | Lessmann | 80/35 |
| 3,461,030 | 8/1969 | Keyes | 162/198 |
| 3,490,689 | 1/1970 | Hart et al. | 162/253 |
| 3,620,915 | 11/1971 | Keyes IV | 162/253 |
| 3,687,802 | 8/1972 | Rummel et al. | 162/253 |
| 3,873,416 | 3/1975 | Forgacs | 162/263 |
| 4,098,641 | 7/1978 | Casey et al. | 162/253 |
| 4,159,639 | 7/1979 | Simms, et al. | 73/63 |
| 4,648,712 | 3/1987 | Brenholdt | 162/49 |

FOREIGN PATENT DOCUMENTS 0200650 12/1986 European Pat. Off. .

OTHER PUBLICATIONS

Ekstrom et al., "Automating the Control Loops on A Swedish Kraft Paper Machine"; *Pulp & Paper*, Apr. 3, 1967.

"The Application of X-Ray Absorption and Fluorescence Analysis to the Measurement of Paper Additives", by Alexander Buchnea, et al., 2211 Int'l Journal of Applied Radiation and Isotopes, vol. 33, Apr. 4, pp. 285-222 Oxford, Great-Britain.

84-067639/11 Paper Res Inst., Week 84, Issued Apr. 25, 1984.

*Primary Examiner*—Steve Alvo
*Attorney, Agent, or Firm*—Spensley Horn Jubas & Lubitz

[57] ABSTRACT

A system and process for continuously determining the strength of paper sheet material during manufacture includes a plurality of sensors for detecting proxies related to properties such as the strength of individual fibers, length distribution of fibers, quantity of fibers, distribution of fibers, orientation of fibers, number of bonds between fibers, and bond strength of fibers. For a given papermaking machine and paper type, multiple regression analysis is used to determine correlations between the measured proxies and laboratory tests of paper strength. Then, during operation of a papermaking machine, changes in the proxy measures are used to indicate paper strength and to adjust operation of the papermaking machine based upon changes in the strength of sheet material being produced.

20 Claims, 5 Drawing Sheets

PROCESS FOR CONTINUOUS DETERMINATION OF PAPER STRENGTH

BACKGROUND OF THE INVENTION

1. Field of the Invention

The present invention relates to the art of papermaking and, more particularly, to the continuous determination of paper strength during manufacture of paper sheet materials.

2. State of the Art

In the papermaking industry, strength specifications are commercially important for numerous paper products including bag paper, liner board, corrugating medium, newsprint, and tissue paper. As a result of custom and developments over the years, strength specifications are usually based upon standardized laboratory procedures for determining properties such as burst strength, tensile strength, elongation, internal tearing resistance, edge tearing resistance, crush strength and so forth. A specific example of a widely accepted laboratory test is the Mullen burst test. A Mullen test is usually conducted by clamping a sample of paper across a ring and then providing a diaphragm to increase pressure against one side of the clamped paper until it bursts. The pressure at which the sample bursts is called the Mullen burst strength test. (Standard specifications for this test include TAPPI 403os-76 and ASTM D774.) Another example of a customary laboratory test procedure is the "STFI" compression test for heavy papers established by the Swedish Technical Forest Institute. In the STFI test, a sample strip is held between a pair of clamps that are moved towards each other while compressive force is monitored; the maximum compressive force is called the STFI compressive strength of the paper. (Standard specifications for this test include TAPPI 78180s-76 and ASTM D1164.)

Still another example of a widely accepted laboratory test is the standardized tensile strength test wherein a sample strip of paper is pulled in opposite directions with progressively increasing force until the sample fails; the tension at the failure point is called the tensile strength of the paper. (Standard specifications for this test include TAPPI Standard T404os-76 and ASTM Standard-D828.)

Laboratory test procedures in the papermaking art, however, have certain inherent limitations. One critical limitation is that substantial periods of time are required for sample acquisition and analysis. During these periods, production conditions may change sufficiently that the laboratory tests results, when available, are no longer representative of current manufacturing or product conditions. Another limitation is that almost all laboratory tests detect physical failure of paper materials and, thus, are necessarily destructive tests. Yet another limitation is that laboratory tests inherently involve sampling, and the relatively small samples obtained for testing may not completely or accurately represent sheet material that has been produced. Because of the above-mentioned limitations and the fact that paper quality laboratories can test only a small fraction of the paper produced by papermaking machines, it often happens that enormous quantities of substandard paper are produced before a quality laboratory discovers production problems.

In an apparent effort to automate laboratory test procedures, U.S. Pat. No. 4,550,613 suggests an apparatus for automatic determination of the tensile strength properties of a sheet of paper. The apparatus includes a cutter to cut a sample of paper of standard width and a device for measuring the tensile strength properties of the sample.

In light of the limitations of standardized laboratory procedures, whether automated or not, workers in the papermaking art have sought to make continuous measurements of paper strength on-line, i.e., while a sheetmaking machine is operating. On-line measurements, if made rapidly and accurately, have the potential to enable nearly immediate control of papermaking processes and, thus, to substantially reduce the quantity of substandard paper that is produced before process conditions are corrected. In other words, on-line measurements have the potential to substantially reduce time delays between the occurrence and correction of "upset" conditions in papermaking processes. In practice, however, on-line measurements of papermaking processes are difficult to make accurately and often cannot be well correlated with standardized laboratory tests.

One of the difficulties in making accurate measurements of sheet material on papermaking machines arises from the fact that modern papermaking machines are large and operate at high speeds; for example, many papermaking machines can produce sheets up to four hundred inches wide at rates, called "wire speed," of about 20 to 100 feet per second. Another complication affecting on-line measurements is that physical properties of paper sheet material can vary across the width of a sheet and may be different in the machine direction than in the cross sheet direction. (Thus, in laboratory tests, paper strength typically has different values depending on whether test strips are cut in the machine direction or the cross direction.)

Because laboratory tests of paper sheet characteristics are normally destructive in nature, such test procedures cannot be readily adapted for obtaining on-line measurements. On the other hand, because commercial custom is such that laboratory tests of sheet properties are the yardstick for acceptability of on-line measurements, only on-line sensors whose outputs correlate well with laboratory tests of sheet properties are likely to have maximum acceptance in the papermaking industry.

One specific example of a suggestion to provide on-line measurement of mechanical properties of paper sheet materials appears in U.S. Pat. No. 4,291,577, assigned to the Institute of Paper Chemistry and entitled "On Line Ultrasonic Velocity Gauge." This patent describes a system for measuring velocities of ultrasound waves through traveling paper webs using a device having spaced-apart wheels that roll along a traveling paper web; the wheels have transducers on their peripheries to impart ultrasound signals to the web. According to the patent, output signals from the transducers can be utilized to measure the velocity of sonic waves through the web. Also the patentee suggests that the sonic velocity measurements can be correlated with Young's elastic modulus which, in turn, can be used to estimate paper strength. (See also Baum, G. A., "Paper Testing and End-Use Performance" printed in "Compressive Strength Development on the Paper Machine", Institute of Paper Chemistry, 5–8, 1984.)

Other workers in the art have also suggested that correlations exist between tensile strength, burst strength and sonic velocity through a paper web. See, "On-line Measurement of Strength Characteristics of a Moving Sheet: Ming T. Lu, TAPPI, 58(6):80 (June 1975). Also see Seth, R. S., and Page, D. H., "The Stress Strain Curve of Paper" in "The Role of Fundamental Research in Paper Making", PIRA Symposium Proceeding, Cambridge, 1981, wherein it is reported that the elastic modulus of a sheet relates to the elastic modulus of the fibers, the mean length and width of the fibers and the relative bonding area. Also see U.S. Pat. No. 4,574,634 that disclosed a device employing sonic transducers to detect the machine direction and cross-direction Young's moduli for paper samples. Further, in U.S. Pat. No. 4,335,603, assigned to Beloit Corporation, it has been suggested that tension in a moving paper web can be detected by measuring the time of travel of a sonic wave through the web.

By definition, Young's modulus indicates the rate of change of a stress-strain relationship. In the relationship as applied to paper materials, stress refers to loading force applied to a paper specimen and strain refers to elongation of the specimen in response to the applied force. It has been observed that, when Young's modulus is determined for a given specimen of paper, the failure point of other paper of the same kind can sometimes be predicted. In practice, however, Young's modulus has not been rigorously related to papermaking process conditions that affect paper strength and it is known that some processing steps may increase the strength of paper of a certain kind with little substantial change in Young's modulus and that other processing steps, such as wet straining, may substantially affect Young's modulus for certain kinds of paper with substantially less effect upon paper strength measures. See, for example, the article by Seth and Page, supra.

As further background to the present invention, it is useful to generally describe a typical papermaking process. Broadly speaking, a papermaking process begins when a slurry of fibers and water, called raw stock, is spread from a reservoir called a "head box" onto a wire mesh that supports the web while allowing substantial drainage. After the wet web of fibers is formed, the web is passed through a press section where water is squeezed from the web and then through a dryer section where water is evaporated from the web. After the dryer section, the web passes through calendar rollers to provide surface finish and then, usually, through a scanner and onto a reel. The portion of a papermaking process prior to a dryer is often referred to as the "wet end" of the process. It can be appreciated that on-line measurements at the wet end are desirable because such measurements, if acted upon promptly, can provide control early enough during paper production to allow process changes before substantial quantities of substandard paper are produced. On the other hand, wet end measurements are difficult to make because of the high water content of paper webs at this stage and because of frequently severe environmental conditions.

Still further as background to the present invention, it should be understood that papermaking machines have been instrumented to include sensors to detect parameters such as wire speed, basis weight, moisture content, and caliper of the paper during production. Many of the on-line sensors are designed to periodically traverse or "scan" traveling webs of sheet material to provide successive measurements across the webs. (In the sheet-making art, a succession of measurements at adjacent locations that, in total, spans a traveling web in the cross direction is called a "profile.") Scanning systems are advantageous because, as mentioned previously, various properties of paper may vary across a sheet as well as along the sheet; particularly, cross-direction strength properties may be different than machine direction strength properties.

Examples of scanning systems are provided in U.S. Pat. Nos. 3,641,349; 3,681,595; 3,757,122; and 3,886,036 assigned to Measurex Corporation. Other specific examples of scanning gauges proposed by workers in the art include ones that detect the composition of sheet material by measuring the radiation absorbed from beams of infrared light or other radiation of known wavelength directed against a given area of the sheet material. Devices of the latter type operate in accordance with the general principal that the amount of radiation absorbed by sheet material at a particular wavelength is a function of the composition of the material. Also, in U.S. Pat. No. 4,453,404 assigned to Mead Corporation, there is described a scanning system for determining statistical characteristics of sheet material; the patent states that the system can monitor the weight basis of sheet material, such as paper, as the material is being produced. Still further, in U.S. Pat. No. 2,806,373 there is disclosed an apparatus for testing sheet paper comprising at least two detectors that are continuously responsive to thickness and opacity variations. The patent states that, for paper produced in a given paper mill from given raw material, relationships exist between various characteristics of the paper and that a knowledge of some of the characteristics permits conclusions to be drawn regarding other characteristics; particularly, the patent states that variations in porosity and moisture can be obtained as algebraic functions of variations of thickness and substance.

Still further as to prior art, it may be noted that U.S. Pat. No. 3,687,802 describes a method and system for controlling the moisture content, mullen, and basis weight of paper by measuring each and developing appropriate control signals for adjusting a papermaking machine so that the desired measurements are approximated. Also, U.S. Pat. No. 3,936,665 discloses a sheet material monitoring apparatus including sensing gauges and a computer for determining a data profile across the sheet material. According to the patent, the monitored data may be used to provide information to control a sheet-making process to obtain a desired characteristic of the sheet material. Further, the patent teaches the data profile of a characteristic of a sheet is to be obtained without using scanning gauges.

OBJECTS AND SUMMARY OF THE PRESENT INVENTION

Generally speaking, a primary object of the present invention is to provide improved systems and methods for continuously determining strength properties of traveling continuous webs of paper sheet material during manufacture on a papermaking machine without destructive testing.

More particularly, an object of the present invention is to provide improved on-line systems and methods for non-destructively detecting process measurement proxies for strength properties of paper sheet materials during manufacture, which proxies can be used, for example, to control changes in papermaking processes to selectively vary the strength of paper sheet material being produced.

In accordance with the preceding objects, the present invention generally provides a non-destructive process and system for continuously determining the strength of paper sheet material during manufacture based upon detection of process measurement proxies for at least four of the following properties relating to sheet strength: the strength of individual fibers, the length distribution of fibers, the quantity of fibers, the distribution of fibers, the orientation of fibers, the number of bonds between fibers, and bond strength. After proxy measures for at least four of the properties are detected, statistical computations are made to correlate the proxy measures with paper strength. Also, operation of the papermaking machine can be controlled based upon changes in the detected proxies to adjust the strength of the produced sheet material.

In a preferred embodiment of the present invention, a process proxy measure for the strength of individual fibers is stress applied to a sheet while drying. Such stresses are detected by, for example, a non-destructive scanning-type device that includes support means for supporting one side of the traveling sheet about a localized unsupported area, deflecting means that displace the sheet within the unsupported area, force sensors for detecting forces related to the force with which said sheet is deflected within said localized area, and displacement sensors for detecting the distance the sheet is deflected within the localized area.

As will become clear from the following description, the methods and systems of the present invention provide substantial advantages in the art of non-destructive detection of strength properties of traveling continuous webs of paper sheet material during manufacture. Additional advantages of the present invention can be ascertained by reference to the following description and attached drawings which illustrate the preferred embodiment.

DETAILED DESCRIPTION OF THE PREFERRED EMBODIMENT

Figure 1:
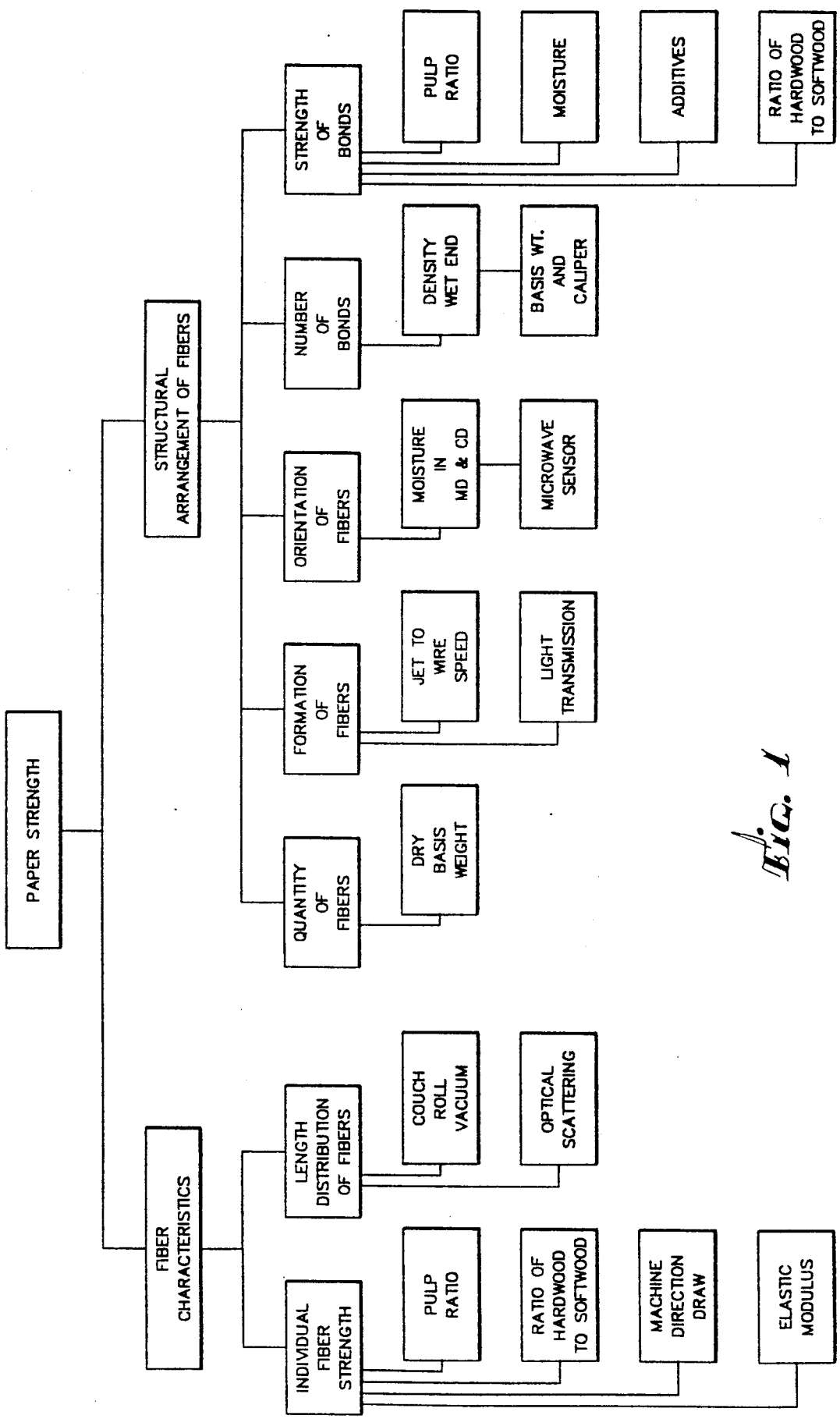
FIG. 1 is a schematic block diagram for a process according to the present invention.

A process for determining paper strength, as generally outlined in FIG. 1, is premised upon identification and detection of process measurement proxies or properties for basic physical properties that determine paper strength. More particularly, based upon the characterization of paper sheets as dried mats of fiber, basic strength properties of paper are classified into two broad categories: properties inherent to fibers, and properties inherent to structural arrangements of fibers. Properties within the first category include the strength of individual fibers and their length distribution. Properties within the second category include the quantity of fibers, their distribution or "formation", their orientation, the number of bonds between fibers, and the strength of the bonds. Still speaking generally, sensors are used in the process outlined in FIG. 1 to provide outputs indicative of process measurement proxies for usually at least four of the basic physical properties that determine paper strength. Consequently, implementation of the process of FIG. 1 provides simplification and rationalization of the art of determining paper strength in a generally continuous manner while paper sheet materials are being produced.

As to sensing the strength of individual fibers, an initial complication is that direct measurements cannot be made without destroying sheet material. This complication, however, is overcome in the process of FIG. 1 by detecting process parameters that are causally correlated with the strength of individual fibers. More particularly, it has been found that the strength of individual fibers primarily depends on fiber species, pulping processes, and stresses applied to sheets while drying. As to fiber species, it has been found that softwoods produce stronger paper than hardwoods, but that paper strength does not substantially vary with particular softwood species. (See Setterholm, V. C., and Chilson, W. A., TAPPI 48, NoII: 634–640, Nov. 1965.) Thus, according to the process outlines in FIG. 1, it is assumed that the ratio of hardwood pulp to softwood pulp provides an indication of paper strength dependent on fiber species. Accordingly, a process measurement proxy for individual fiber strength is provided by tracking the ratio of hardwood to softwood in a pulp, usually through flow measurements.

Further as to indirect measures of the strength of individual fibers, it is known that differences in pulping processes affect fiber strength. For example, see Mardon, J., et al, "Stock Quality Factors Affecting Paper Machine Efficiency", Technical Section CPPA, Montreal, 1972, wherein it is reported that increasing chemical pulp in newsprint paper increases strength and the elastic modulus of the newsprint. Typical pulping processes include groundwood, thermo-mechanical, and kraft processes. Many common paper materials, including newsprint, are produced by mixing pulps produced by two or more pulping processes. Thus, another process measurement proxy for individual fiber strength is provided by detecting the quantity ratio of pulps fed to a papermaking machine (i.e., the pulp ratio). The pulp ratio can ordinarily be detected through simple flow monitoring.

Still further as to indirect measures of the strength of individual fibers, it has been shown that stress applied during drying may increase the strength of individual fibers in sheet material. See C. Kim et al, "The Mechanical Properties of Single Wood Pulp Fibers", Journal of Applied Polymer Science, Vol. 14, pp. 1549–1561 (1975). This effect is most likely caused by wet fibrils sliding past one another during drying to relieve areas of non-uniform stress concentrations. One manifestation of this effect is that, because of mechanically-induced draw or elongation of paper in the machine direction during production, paper is often anisotropic in the sense that it is stronger in the machine direction than in the cross direction. As indicated in FIG. 1, machine-direction draw (i.e., elongation) can be detected as a process measurement proxy for individual fiber strength. In practice, machine-direction draw is readily detected by conventional velocity sensors or tachometers attached to selected rolls on a papermaking machine.

Further, it has been found that stresses build in paper sheets during drying because of paper shrinkage and machine draw and because of restrictions on physical movement of the sheets. It has also been found that the cross-direction elastic moduli decrease from the center toward the edges of sheets on papermaking machines. Such findings form a basis for use, in the process outlined in FIG. 1, of measurements related to elastic moduli as process measurement proxies for stress. A sensor device for detecting the cross-direction and machine direction elastic moduli is described in conjunction with FIGS. 2 through 6.

Referring still to the process in FIG. 1, the second property within the fiber characteristics category affecting the strength of paper sheet materials is fiber length distribution. This property is important to sheet strength because it has been shown that long fibers produce more bonds per fiber than short fibers. One process measurement proxy for fiber length distribution is vacuum on a couch roll of a papermaking machine. An explanation for the basis for this measurement proxy is that sheet porosity, as indicated by couch roll vacuum, decreases with fiber length because short fibers more frequently plug open areas in sheets than long fibers. Another measurement proxy for the length distribution of fibers is optical scattering. An explanation for the basis for this measurement proxy is that light incident on sheet materials is scattered more by short fibers than long fibers. In practice, optical scattering can be detected by various conventional infrared scanning devices such as the infrared Measurex Moisture Sensor manufactured by Measurex Corporation of Cupertino, Calif.

Measurement of properties within the category of structural arrangement of fibers will now be described in terms of the process outlined in FIG. 1. One of the properties within this category is quantity of fibers. Identification of this property as affecting sheet strength is based upon observations indicating that the strength of fibrous sheets is generally proportional to the number of fibers within the sheets. As indicated in FIG. 1, a process measurement proxy for the quantity of fibers in a sheet is provided by detecting the dry basis weight of the sheet. Dry basis weight is normally defined as the weight per unit area of sheet material excluding moisture, and is usually stated in units of grams per square meter; thus, in the art of papermaking, dry basis weight is equivalent to the weight of dry material, primarily fibers, comprising a given area of a paper sheet. Related measurement parameters are basis weight and moisture content of a sheet per unit area; such parameters are related by the fact that, for a given area of a sheet, dry basis weight equals basis weight minus moisture content.

Dry basis weight can be determined by using a Measurex Basis Weight Sensor in conjunction with a Measurex Moisture Sensor and a Measurex X-ray Ash Sensor; the latter two devices measure moisture and filler content, respectively. With such measurements, dry basis weight can be calculated by subtracting the moisture and filler content from total basis weight. Also, U.S. Pat. No. 4,289,964, assigned to Intec Corporation, suggests that beta ray gauges can scan across a traveling web in the cross direction to determine basis weight. Further, a device for measuring dry basis weight is taught in U.S. patent application Ser. No. 902,225, filed Aug. 29, 1986, now U.S. Pat. No. 4,767,935 and commonly assigned to Measurex Corporation of Cupertino, Calif. The device described in the application optically measures dry basis weight of sheet materials by reflecting rays of light onto one surface of a traveling paper web and then detecting two distinct light wavelengths transmitted through the web.

In the sheet-making art, the distribution of fibers within a sheet is referred to as "formation." Formation can be related to sheet strength because it is known that sheets with different fiber formations have substantially different strengths and that sheets with non-uniform fiber formations are weakest at areas, called "thin spots", where fiber concentrations are minimal. Generally speaking, a process measurement proxy for fiber formation can be obtained by optically detecting the transmission of collimated light through a traveling sheet using optical sensors that are relatively insensitive to moisture variations; examples of suitable optical sensors include ones that measure the transmission through sheet material of highly collimated light at narrow bands of wavelengths about 1.3 microns. With such optical sensors, thin spots are identified as transmission maxima.

An alternative process measurement proxy for fiber formation is the ratio of jet to wire speed, where jet speed is the speed at which pulp exits a head box. The justification for this measurement is that turbulence destructive to fiber floc formation is created at jet speeds slower than wire speeds. Wire speed also affects formation because increases in wire speed normally require increases in jet speed. Jet speed can be detected from conventional measurements of head pressure, and wire speed can be detected by conventional tachometers connected to appropriate rolls in a papermaking machine.

At this juncture, it may be noted that U.S. Pat. No. 3,435,242 discloses a device that is said to inspect the formation of fibers in sheets of paper. The device includes a plurality of narrow-beam photodiodes that are placed proximate to the material to be tested, a narrow-beam detector, and an instantaneous ratio computer to provide output signals representing the structural formation of the tested material. Also, in the publication "Pulp & Paper" (Aug. 1985, p. 163) there is described a device called the Lippke sensor to monitor sheet formation or fiber orientation at the wet end of a papermaking process; the Lippke sensor is said to employ a laser light beam and a two-dimensional photodetector to detect the light scattering differential between randomly oriented fibers and fibers oriented parallel to one another.

Further with regard to FIG. 1, the detection of geometrical orientations of fibers will be described. In this regard, it should be understood that sheet strength has been found to be greater in the direction of orientation of the majority of fibers within a sheet than in other directions. To provide process measurement proxies for fiber orientations, a system comprising two microwave moisture sensors can be utilized with one of the sensors oriented in the machine direction and the other in the cross direction. Also, in U.S. Pat. No. 3,807,868 assigned to Valmet Oy, there is described a method for determination of fiber orientation in paper including the steps of detecting polarized light at right angles to the plane of the paper, reflecting the light in two planes at right angles to each other, and forming two quantities based upon the reflected light to provide an index value for the anisotropy of fiber orientation. Further, in an article by Z. Koran et. al. entitled "Network Structure and Fiber Orientation in Paper", TAPPI Journal, May 1986 (pp. 126–128), there is described a method for detecting fiber orientation in paper by X-ray diffraction and zero-span tensile testing. Notwithstanding the foregoing, however, it should be mentioned that fiber orientation is normally a function of head box design and, although headbox designs can vary substantially from machine to machine, the effect of headbox design on fiber orientation is generally constant for a given machine.

Still another property affecting paper strength is the number of bonds formed by fibers within a sheet. Because the number of bonds within a paper sheet generally increases as fibers are packed more densely together, density measurements can provide a process measurement proxy for the number of bonds between fibers. For purposes of the process outlined in FIG. 1, density measurements should be made at the wet end of a papermaking process because, at the dry end, calendering increases density but may weaken the sheet material by mechanically breaking down fibers. In practice, density can be directly detected on-line using conventional sensors for determining basis weight and caliper.

As to the strength of bonds between fibers, it has been found that bond strength primarily depends on fiber species, pulping processes, additives, pressure, and moisture. The relationship of bond strength to fiber species is essentially the same as the relationship of individual fiber strength to fiber species, namely that stronger bonds are provided by softwoods than hardwoods but that bond strength is substantially independent of particular hardwood species or softwood species so long as the ratio of hardwood pulp to softwood pulp is maintained constant. Thus a process measurement proxy for individual bond strength is provided by monitoring the ratio of hardwood to softwood in feed pulp, usually through flow monitoring devices. Also, as in the case of fiber strength, bond strength varies as a function of the pulp ratio of feed to a papermaking machine; again, this proxy measure can be detected by conventional flow monitoring devices.

In papermaking processes, additives such as gum or starch are sometimes used to increase bond strenght. When such additives are used, the quantity of the additives can be measured by flow measurement devices and calibrations can be made to reflect the effectiveness of the additives on the strength of bonds between fibers.

Further as to the strength of bonds between fibers, it is known that wet pressing increases bond strength by increasing the contact area between fibers and allowing more bonds to form. In practice, most wet pressing is accomplished by crown rolls that operate at constant pressure. Thus, although wet pressing can affect bond strength, such processing is not usually variable and, therefore, does not require constant monitoring as a factor affecting sheet strength.

The moisture content of fibrous sheet material also affects bond strength and is primarily determined by dryer temperature and wire speed. In practice, the moisture content of sheet materials is readily measured on-line with conventional moisture sensors such as the aforementioned Measurex moisture sensor. As indicated in FIG. 1, the detected moisture content of sheet material can be used to indicate the strength of fiber bonds and, hence, the strength of the sheet material.

The relative contribution of each of the above-mentioned process measurement proxies to the strength of a particular paper sheet material generally depends upon characteristics of the papermaking machine in which the sheet material is formed. For purposes of process control of an individual machine, some of the process measurement proxies can often be considered to be invariant. For instance, although orientation of fibers affects paper strength and can be determined by head box design, the effects of head box design are usually constant during operation of modern papermaking machines and, therefore, can usually be accounted for by instrument calibration and need not be continuously measured.

Figure 7:
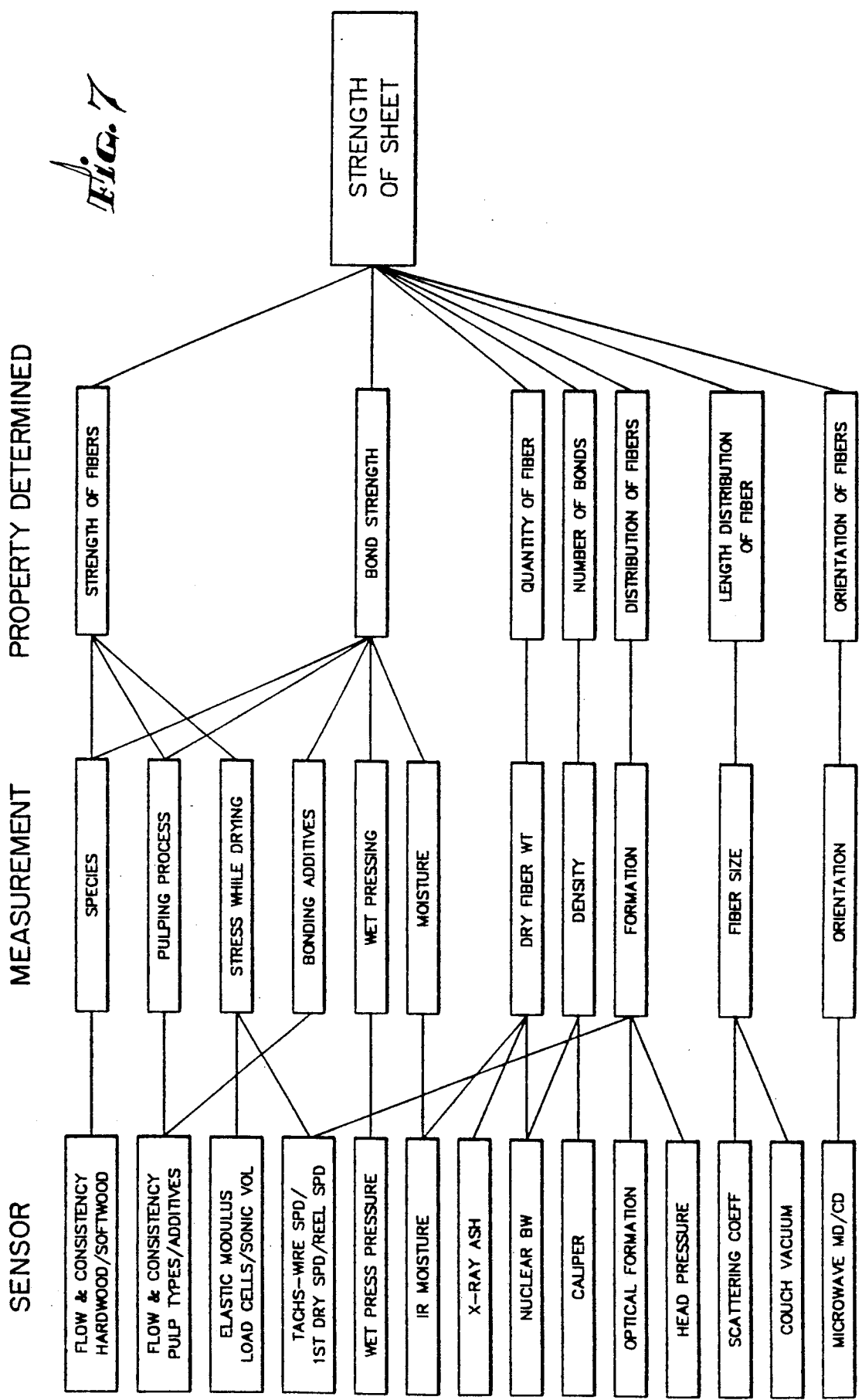
FIG. 7 is a diagram that illustrates the interrelationship of measurements obtained by various sensors, including the sensing device of FIGS. 2 and 3, for determination of paper sheet strength in terms of the process outlined in FIG. 1.

FIG. 7 provides a diagram of the interrelationship of process measurement proxies and parameter sensors to the determination of paper sheet strength. It should be noted that the seven properties listed in FIG. 7 are the same as the ones discussed with respect to FIG. 1. Further, FIG. 7 indicates types of sensors that can be used to provide process measurement proxies that determine the seven properties. For example, an infrared (IR) moisture sensor can be employed to detect the moisture content of a traveling sheet and, hence, to provide a measure of bond strength between fibers. It should be noted that a particular type of sensor can be used to provide more than one process measurement proxy; for example, an IR moisture sensor can be used to indicate both moisture content and dry fiber weight.

Figure 2:
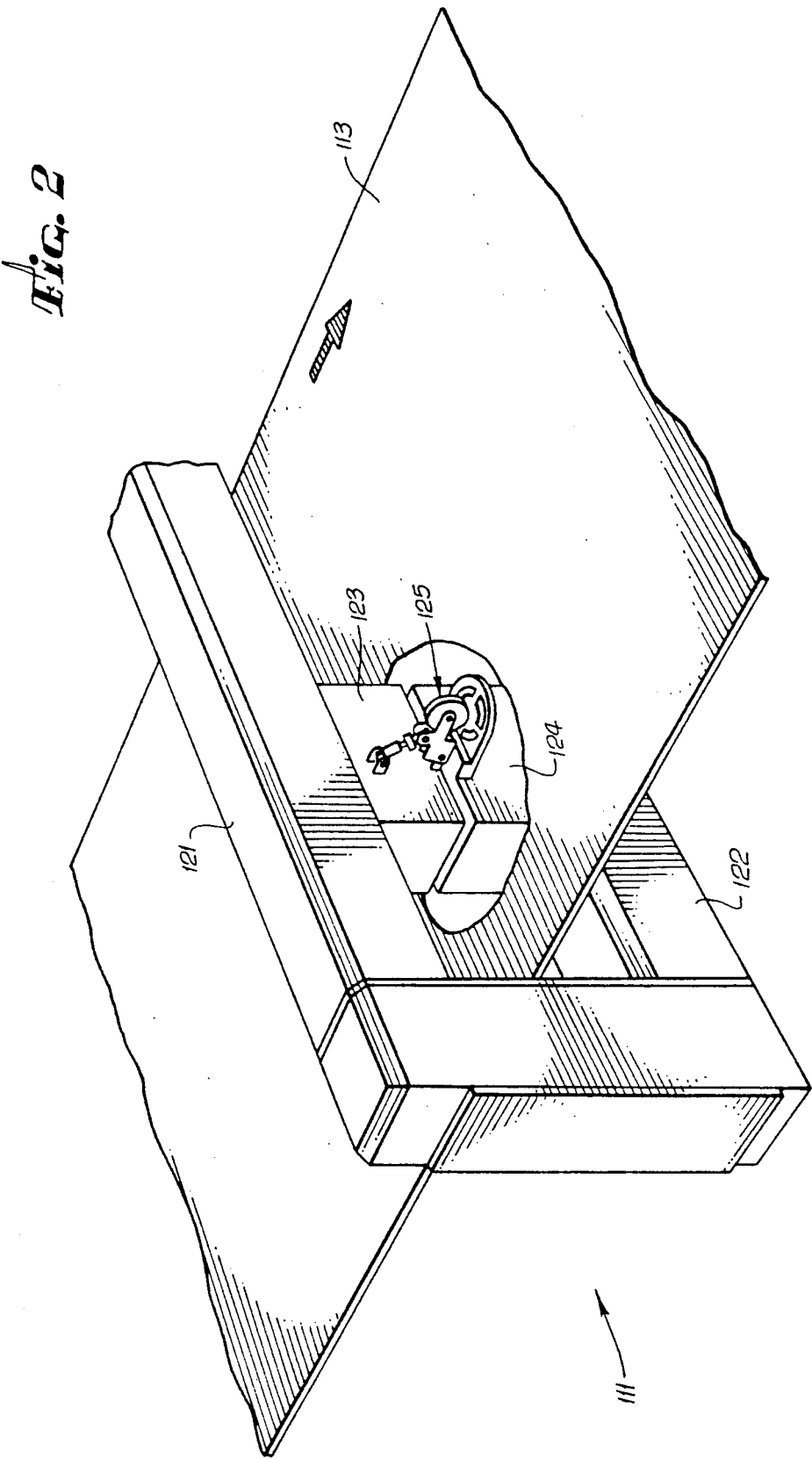
FIG. 2 is a pictorial view of an example of a scanning-type sensing device for use in a process and system according to the present invention to continuously determine strength of paper sheet material.

Referring now to FIG. 2, there is shown a scanning station, generally designated by the number 111, that extends across a paper web 113 in the cross direction and that includes a sensor for detecting stress in web 113. In the particular embodiment of scanning station 111 chosen for illustration, web 113 passes horizontally between a pair of stationary parallel beams 121 and 122 that are mounted to extend transversely across the web parallel to its opposite faces. Depending upon the papermaking machine, beams 121 and 122 can range in length from about 100 inches to about 400 inches. Normally, scanning station 111 is located at a position on a papermaking machine where paper motion is relatively stable and not subject to substantial variations, such as flutter.

As further shown in FIG. 2, scanning station 111 includes traveling carriage devices 123 and 124 that are mounted on upper and lower beams 121 and 122, respectively, to scan web 113. (In FIG. 2, web 113 is shown with a cut out area so that the lower carriage device 124 is not obscured.) A conventional drive mechanism, not shown, is provided to drive carriage devices 123 and 124 back and forth along beams 121 and 122. In operation, the drive mechanism functions to operate carriage devices 123 and 124 in synchronization, with one always aligned opposite the other.

Figure 3:
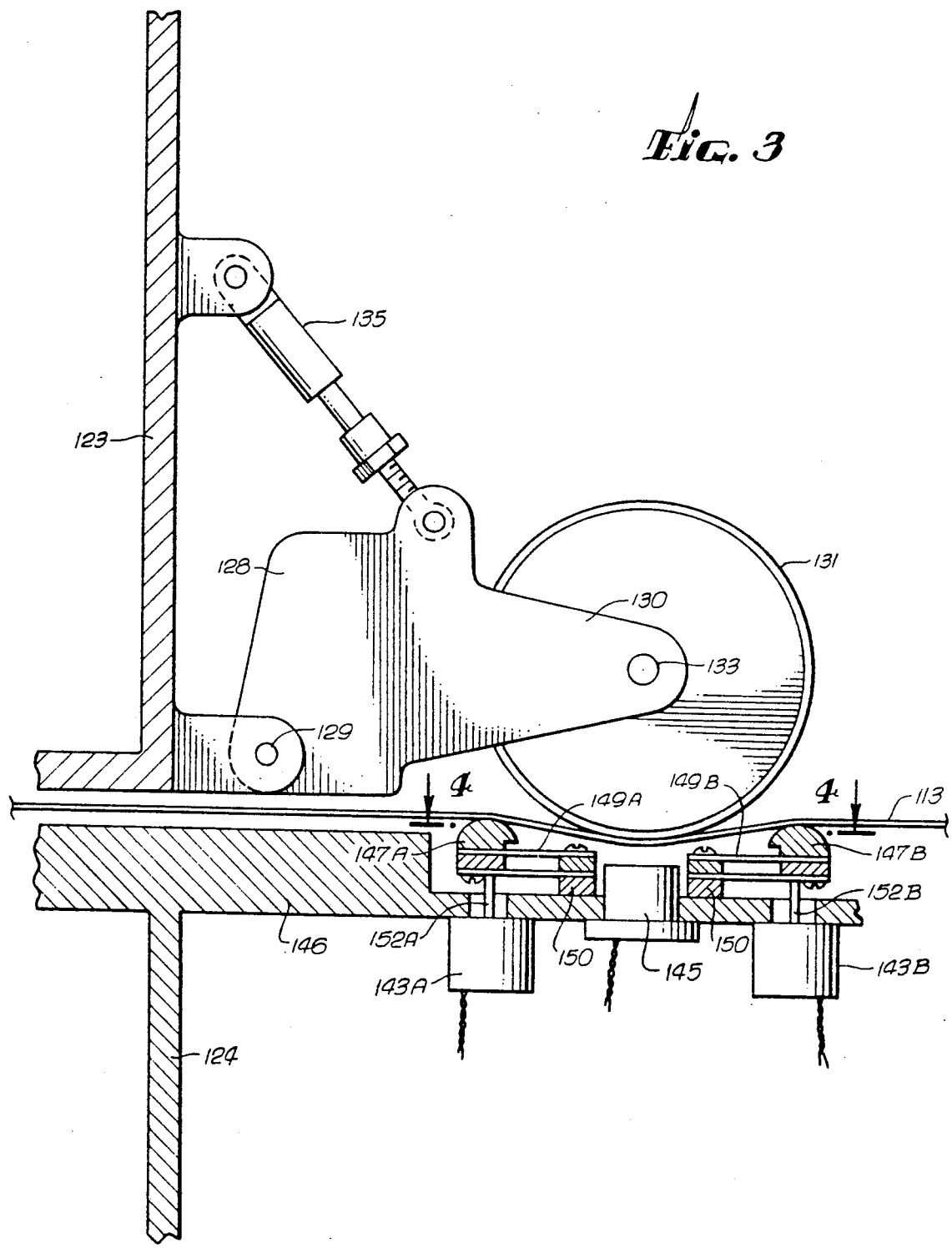
FIG. 3 is a side view, partially in cross-section, of the sensing device of FIG. 2.

Also in connection with FIG. 2, it should be noted that upper carriage device 123 carries one part of a sensor, generally designated by the number 125, and that lower carriage device 124 carries another part of the same sensor; the complete sensor 125 is shown in FIG. 3. Generally similar sensors are shown in the following U.S. Patent Applications assigned to Measurex Corporation of Cupertino, Calif.: Ser. No. 730,406 filed May 2, 1985; Ser. No. 784,213 filed Oct. 4, 1985 (now U.S. Pat. No. 4,864,581); and U.S. patent application filed July 18, 1986 as a continuation-in-part of application Ser. No. 784,213, now abandoned and refiled as Ser. No. 195,364, filed May 13, 1988 (now U.S. Pat. No. 4,866,984).

Referring now to FIG. 3, the structure of the upper portion of sensor 125 will be described first. The upper portion comprises a clevis-like bracket 128 having U-shaped legs 130. Bracket 129 is coupled to carriage device 123 by a horizontal pivot pin 129 that allows the bracket to pivot vertically relative to the surface of web 113. A wheel 131 is mounted to rotate freely on a horizontal axle 133 extending between U-shaped legs 130 and is dimensioned to ride on the surface of web 113. Pivotal motion of bracket 128 in the vertical direction is limited by an air cylinder 135 that is pivotably linked between carriage 123 and the bracket. Air cylinder 135 is normally provided with compressed air at sufficient pressure to keep wheel 131 positioned against the surface of web 113 at a generally fixed location in the vertical direction.

Figure 4:
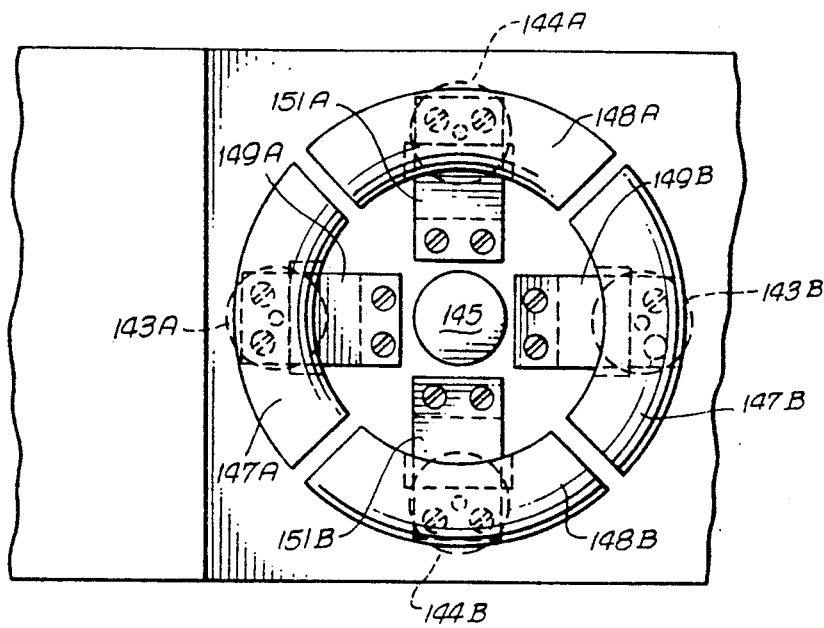
FIG. 4 is a plan view of the lower portion of the sensing device of FIG. 3 taken along the plane of the line 4—4 in FIG. 3 for viewing in the direction of the arrows.

The lower portion of sensor 125, as shown in FIGS. 3 and 4, generally includes at least two pairs of force sensors, designated in the drawings as pair 143A and 143B and pair 144A and 144B, and a displacement sensor 145. The force sensors and the displacement sensor are all rigidly connected to a plate 146 fixed to lower carriage device 124. Further, as shown in FIGS. 3 and 4, the lower portion of sensor 125 includes pairs of contact members 147A and 147B, and 148A and 148B, respectively, which are so named because they are in contact with the undersurface of web 113. In the illustrated embodiment, contact members 147A and 147B are mounted at the free ends of an associated pair of flexible cantilever members 149A and 149B, respectively, whose opposite ends are stationarily mounted to plate 146 by spacers 150. Similarly, contact members 148A and 148B are mounted to the free ends of an associated pair of flexible cantilever members 151A and 151B whose other ends are stationarily mounted to plate 144 by spacer members (not shown). The pair of contact members 147A and 147B are aligned in the machine direction and will be referred to herein as the machine-direction pair; likewise, the pair of contact members 148A and 148B are aligned in the cross-direction, and will be referred to herein as the cross-direction pair.

As best shown in FIG. 3, the machine-direction pair of contact members 147A and 147B are connected to respective force sensors 143A and 143B by pin members 152A and 152B, respectively, such that displacement of the contact members exerts forces on the sensors via vertical movement of the pin members. It should be understood that the cross-direction pair of movable contact members 148A and 148B are similarly connected to force sensors 144A and 144B, respectively. In practice, the force sensors are conventional piezo resistance devices or strain gauges that provide electrical output voltages proportional, preferably linearly, to the force exerted on the cells. Also in practice, displacement sensor 145 is a conventional proximity sensor that provides output voltages that are proportional, again preferably linearly, to the distance between the displacement sensor and the surface of web 113.

Operation of sensor 125 of FIGS. 2 through 4 will now be generally described. Initially, it should be assumed that sensor 125 is assembled such that both the machine-direction pair and the cross-direction pair of contact members are located to press against the undersurface of web 113 and so that wheel 131 is in contact with the surface of web 113 at a point generally midway between the contact members of the respective pairs and generally directly above displacement sensor 145. Also, for purposes of understanding the preferred mode of operation of sensor 125, it should be assumed that cylinder 135 is pressurized sufficiently that wheel 131 can be considered to have a fixed location in the vertical direction. In such an assembly, force sensors 143A and 143B function to detect the amount of force with which traveling web 113 presses against movable contact members 147A and 147B, and displacement sensor 145 detects changes in the position of the surface of web 113 relative to plate 146.

Further operation of sensor 125 will be explained in conjunction with FIG. 5. In that diagram, dimension "d" indicates the horizontal distance from the point of contact of wheel 131 with the surface of web 113 to the point of contact of one of the movable contact members, say member 147B, with web 113. Dimension "z" indicates the vertical distance that the surface of web 113 is displaced by wheel 131. Although dimension "z" is constant ideally, it will vary somewhat in actual operation of scanning sensor 125 due to mechanical flexure of the sensor. To compensate for such variations, the value of "z" is monitored by displacement sensor 145 and a signal whose amplitude is representative of the distance "z" is provided at the output of the sensor. Knowing the detected values for "z" and "d", dimension "h" can be determined. Geometrically, dimension "h" represents the hypotenuse of a triangle whose legs are "d" and "z", respectively, and can be understood to be generally collinear with the surface of web 113 that extends from the selected contact member to the point of contact with wheel 131.

Figure 5:
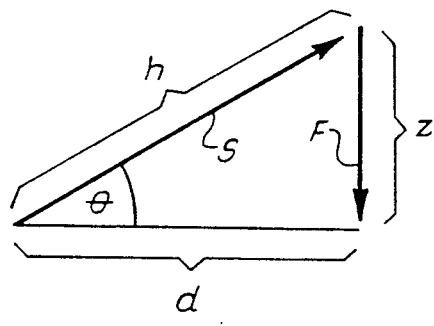
FIG. 5 is a diagram that will be used to assist in explaining operation of the sensing device of FIGS. 2 and 3.

For a given draw of web 113, the stress in web 113 along distance "h" can be detected as a function of the force exerted by web 113 on one of the force sensors 143A, 143B, 144A or 144B. Thus, if variable "S" represents the stress in web 113 along distance "d" and if "F" designates the force sensed by one of the sensors when wheel 131 is in contact with web 113, the relationship between S and F can be resolved by a force triangle and can be expressed as:

$$S \sin \theta = F$$

where $\theta$ is the angle between "d" and "h" as indicated in FIG. 5. The above equation can be rearranged to be:

$$S = F / \sin \theta.$$

Since $\sin \theta$ is nearly equal to $\tan \theta$ for small angles, the relationship between S and F can be expressed by the approximation:

$$S = F / \tan \theta.$$

Because $\tan \theta$ is the ratio of "z" to "d", the stress S in web 113 can be expressed as:

$$S = \frac{Fd}{z}.$$

Thus, for practical purposes, the stress in web 113 can be understood to be a function of three measured properties: the displacement (z) of web 113, the placement (d) of wheel 131 relative to a force sensor, and the force (F) detected by one of the force sensors.

In practice, the forces applied to the machine-direction pair of force sensors 143A and 143B are not necessarily the same as the forces applied to the cross-direction pair of force sensors 143C and 143D because of differences in stresses and tension in the machine direction and the cross direction. As a result of these differences, different strengths can be determined for web 113 in the cross direction and in the machine direction. It may also be noted that, in the cross direction, a sheet is restrained but is not usually subject to substantial draw. Nevertheless, sensor 125 can provide meaningful strength measurements in the cross direction because it, in essence, induces localized stress by displacement of the surface of the sheet by wheel 131.

An alternative mode of operation of sensor 125 will now be described wherein cylinder 135 is pressurized and controlled such that wheel 131 is movable and presses downward against web 113 with a generally constant force such that web 113 is displaced only a relatively small distance toward displacement sensor 145 when web 113 is under normal tension. In such a mode of operation, displacement sensor 145 again detects changes in position "z" of the surface of web 113 relative to plate 146 and, generally speaking, position "z" varies as a function of the stress "S" of web 113. Thus, under practical operating conditions, the stress in web 113 can again be expressed as a function of three measured properties: the displacement (z) of web 113, the placement (d) of wheel 131 relative to a selected force sensor, and the force (F) detected by a selected one of the force sensors.

The stress measurement "S", as detected through the above-described operation of sensor 125, can be used to predict strength properties of web 113 in conjunction with the detection of process measurement proxies according to FIG. 1. The relationship of stress "S" to the process measurement proxies will now be explained in terms of the graph in FIG. 6, whose vertical axis represents stresses applied to a given area of web 113 by sensor 125 and whose horizontal axis represents the strain on the same section of the web. Here again, strain can be interpreted to be elongation or "draw" of web 113 and can be measured in the machine direction by continuously monitoring the velocity of rollers over which the web travels. In the cross direction, draw is normally constant across a sheet and, therefore, need not be monitored.

Figure 6:
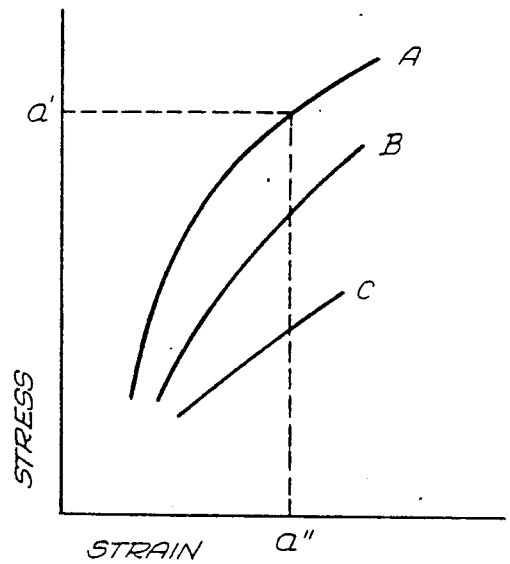
FIG. 6 is a graph that will be used to further assist in explaining the operation of the sensing device of FIG. 3.

In FIG. 6, the curves A, B and C illustrate stress-strain relationships for various types, or grades, of paper. Thus, curve "A" depicts the relationship between stress that is applied to a particular type of paper and the elongation of that paper. Likewise, curve "B" represents the relationship between stress applied to another type of paper and elongation of that paper. Comparing paper types or grades A and B, it can be seen that a given stress on paper B will create more elongation than the same stress on paper A. The end points of the curves A, B and C are failure points, (i.e., points at which the papers break) and, therefore, indicate the strengths of the paper types. Again comparing paper types A and B, it can be seen that paper type B is weaker than paper type A since it breaks at a lower applied stress. Further with regard to FIG. 6, it should be understood that the slope of the curves A, B and C represent Young's modulus for various grades of paper; for example, the slope of curve A at point "a" is Young's modulus for that grade of paper.

The failure points for the paper grades described by the curves in FIG. 6 are normally determined empirically, which is to say by standardized laboratory methods. In practice, a reliable correlation can often be obtained between laboratory results for various standardized methods. For example, highly reliable correlations have been obtained for standardized laboratory tests such as standardized tensile, STFI compressive and Mullen burst pressure tests.

Because samples of the same grade of paper have generally the same stress-strain relationship, it can be understood from FIG. 6 that grade can be identified for a given paper if stress and strain are measured. For example, if stress point a' and strain point a" are measured for a given paper, the point "a" can be determined and, further, the sample can be identified as having stress-strain properties unique to the paper grade depicted, in such an instance, by curve "A".

It should be further understood that the failure points for the paper grades as depicted by curves A, B and C in FIG. 5 are not necessarily constant for a given paper grade but, instead, can vary depending upon the physical properties discussed in conjunction with FIG. 1 (i.e., fiber characteristics and the structural arrangement of fibers). In practice, for a given papermaking machine and paper grade, functional relationships of sheet strength to the process measurement proxies can be determined using empirical methods and techniques of multiple regression analyses as will be discussed in the following.

Figure 8:
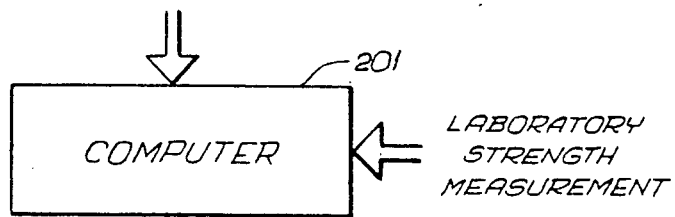
FIG. 8 is a block diagram of a system employing process measurement proxies to provide output signals to control a papermaking machine.

FIG. 8 shows a system that provides output signals for control purposes based upon the process measurement proxies. In FIG. 8, signals that represent at least four of the seven process measurement proxies are indicated as being fed to a computer 201. For the sheet material being produced, computer 201 also receives input indicating strength properties as determined by standard quality laboratory techniques. Computer 201 can be understood to be a conventional digital computer that is programmed with algorithms for multiple regression analyses. Because the process measurement proxy information is normally in analog form, such information must usually be digitized for use by computer 201. Such digitizing can be performed by conventional analog-to-digital converter devices, not shown. With the inputs indicated and when conventionally programmed with correlation and regression algorithms, digital computer 201 operates to determine correlations between the process measurement proxies and laboratory-determined strength values at selected locations in the cross direction of web 113.

Once functional relationships employing the process measurement proxies are determined by computer 201 of FIG. 8, papermaking can be controlled by monitoring the process measurement proxies. For example, after a particular grade of paper is identified, sensor 125 operates in conjunction with other selected sensors to provide process measurement proxies as digital input signals to computer 201 which, ultimately, provides output signals that indicate changes in the strength of web 113. That is, computer 201 can provide output signals representative of deviations of the calculated strength of the sheet material being produced from the desired strength value at each of the cross section locations. The output signals can also be employed to control the papermaking machine by causing adjustments to be made at various cross section locations.

Although the system of FIG. 8 can provide meaningful measures of the strength of web 113 using fewer than all seven of the properties listed in FIG. 7, independent process measurement proxies for at least four of the properties normally must be obtained to provide adequate accuracy for control purposes in processes involving substantially changing conditions. To obtain functions of the process measurement proxies, conventional techniques of standard regression analysis are employed. One form of such a regression equation is, for example, the following "Mullen" strength equation:

$$S_{mu} = A*(JW) + B*(VAC) + C*(S) + D*(MOI) + E*(\% \text{ CHEM}) + F(BW) + G*(\rho) + H$$

where:
$S_{mu}$ is the "Mullen" strength of the paper;
A, B, C, D, E, F, G, and H are regression fit constants;
JW = jet-wire speed;
VAC = couch vacuum;
S = tension in the web;
MOI = percent moisture;
% Chem = percent chemical pulp;
BW = basis weight; and
$\rho$ = density.

The values of the constants A through H in the preceding equation generally depend on the particular papermaking machine and grade of paper. If paper grade is changed substantially, then the constants must normally be recalculated.

According to the preceding equation, Mullen strength can be calculated at selected cross-direction locations by scanning across a web during production. A set of Mullen strength data for a complete scan of a web provides a "profile" of the web. For process control purposes, it is normally important to identify the cross direction location of each component measurement of a profile.

In practice, strength profile measurements obtained in the manner described above provide control advantages during startups, grade changes, and process upsets. Also, the strength profile measurements can be used to reduce sheet variations in the machine direction during steady-state operation by, for example, providing control signals to adjust draw in the machine direction. As another example, such strength profile measurements can be used during newsprint production to provide adjustments for the feed mixture ratio of groundwood to chemical pulp to control paper strength and to increase paper production rates. Also, the above-described system and method can provide arbitrary indexes of strength that allow strength comparisons between paper products independently of standardized systems.

Although the present invention has been described with particular reference to preferred embodiments, such disclosure should not be interpreted as limiting. Various alterations and modifications to the preferred embodiments will no doubt become apparent to those skilled in the art after having read the preceding disclosure. It is intended that the appended claims be interpreted as covering all alternative embodiments and equivalents as fall within the spirit and scope of the present invention.

I claim:

1. A process for detecting the strength of continuous paper sheet material during manufacture by detecting parameters indicative of at least four of the following properties: (a) the strength of individual fibers, (b) the length distribution of fibers, (c) the quantity of fibers, (d) the distribution of fibers, (e) the orientation of fibers, (f) the number of bonds between fibers, and (g) the bond strength of fibers, the process comprising the steps of:
    (i) sensing the parameters for at least four of said properties during manufacture of paper sheet material in a papermaking machine;
    (ii) for the selected papermaking machine and paper grade, calculating correlations of said at least four parameters with laboratory tests of paper strength; and
    (iii) during production of paper on the papermaking machine, nondestructively sensing the at least four parameters and, based upon the determined correlations, calculating the predicted strength of paper being produced by the papermaking machine.

2. A process as defined in claim 1, wherein the step of nondestructively sensing the parameter indicative of the strength of individual fibers includes detecting the ratio of softwood to hardwood in pulp fed to the papermaking machine.

3. A process as defined in claim 1, wherein the step of nondestructively sensing the parameter indicative of the strength of individual fibers includes detecting the ratio of different pulps fed to the papermaking machine.

4. A process as defined in claim 1, wherein the step of nondestructively sensing the parameter indicative of the strength of individual fibers includes detecting draw in the machine direction.

5. A process as defined in claim 4, wherein the step of nondestructively sensing the parameter indicative of the strength of individual fibers further includes detecting stress applied to drying fibers.

6. A process as defined in claim 5 wherein the step of detecting stress applied to drying fibers includes detecting the elastic modulus in the cross direction and in the machine direction.

7. A process as defined in claim 1, wherein the step of nondestructively sensing the parameter indicative of the length distribution of fibers includes detecting couch roll vacuum on the papermaking machine.

8. A process as defined in claim 1, wherein the step of nondestructively sensing the parameter indicative of the length distribution of fibers includes detecting optical scattering of infrared light directed against the sheet material.

9. A process as defined in claim 1, where in the step of nondestructively sensing the parameter indicative of the quantity of fibers includes detecting the dry basis weight of paper sheet material on the papermaking machine.

10. A process as defined in claim 1, wherein the step of nondestructively sensing the parameter indicative of the distribution of fibers includes detecting the transmissivity of the paper sheet material.

11. A process as defined in claim 1, wherein the step of nondestructively sensing the parameter indicative of the distribution of fibers includes detecting the jet to wire speed ratio for the papermaking machine.

12. A process as defined in claim 1, wherein the step of nondestructively sensing the parameter indicative of the orientation of fibers includes detecting moisture in both the machine direction and cross direction on the papermaking machine.

13. A process as defined in claim 1, wherein the step of nondestructively sensing the parameter indicative of the number of bonds between fibers includes detecting the density of the paper sheet material on the papermaking machine.

14. A process as defined in claim 13 wherein density is detected by measuring basis weight and caliper of sheet material being produced on the papermaking machine.

15. A process as defined in claim 1, wherein the step of nondestructively sensing the parameter indicative of the strength of bonds between fibers includes detecting the ratio of different pulps fed to the papermaking machine.

16. A process as defined in claim 1, wherein the step of nondestructively sensing the parameter indicative of the strength of bonds between fibers includes detecting the ratio of softwood to hardwood in pulp fed to the papermaking machine.

17. A process as defined in claim 1, wherein the step of nondestructively sensing the parameter indicative of the strength of bonds between fibers includes detecting the moisture content of the sheet material being produced by the papermaking machine.

18. A process as defined in claim 1, wherein the step of nondestructively sensing the parameter indicative of the strength of bonds between fibers includes detecting the quantity of additives in pulp fed to the papermaking machine.

19. A process as defined in claim 6 wherein the step of detecting the elastic modulus is accomplished by a scanning-type sensor device that includes support means for supporting one side of said traveling sheet about a localized unsupported area, deflecting means for displacing said sheet within said localized unsupported area, first sensing means for detecting forces related to the force with which said sheet is deflected within said localized area, and second sensing means for detecting the distance the sheet is deflected within the localized area.

20. A process as defined in claim 19 further including the step of correlating output signals from said first and second sensing means with a standardized measure of strength of the sheet material at selected locations in the cross-direction.

* * * * *